(12) United States Patent
Yaoi et al.

(10) Patent No.: US 8,976,924 B2
(45) Date of Patent: Mar. 10, 2015

(54) X-RAY CT APPARATUS AND X-RAY DETECTOR

(75) Inventors: Yoshiaki Yaoi, Nasushiobara (JP); Seiichiro Murai, Yokohama (JP); Akihiko Taniguchi, Yokohama (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 110 days.

(21) Appl. No.: 13/089,892

(22) Filed: Apr. 19, 2011

(65) Prior Publication Data

US 2011/0255659 A1 Oct. 20, 2011

(30) Foreign Application Priority Data

Apr. 20, 2010 (JP) ................. 2010-097329

(51) Int. Cl.
- *A61B 6/03* (2006.01)
- *A61B 6/00* (2006.01)
- *G01T 1/164* (2006.01)

(52) U.S. Cl.
CPC ............... *A61B 6/032* (2013.01); *A61B 6/4291* (2013.01); *G01T 1/1644* (2013.01)
USPC .......................................... 378/19; 378/98.8

(58) Field of Classification Search
CPC ........ A61B 6/032; A61B 6/4291; G01T 1/20; G01T 1/2002
USPC ............................ 378/19, 98.8, 147, 149, 154; 250/370.11, 370.09
See application file for complete search history.

(56) References Cited

U.S. PATENT DOCUMENTS

| | | | | |
|---|---|---|---|---|
| 4,982,096 A | * | 1/1991 | Fujii et al. | 250/370.11 |
| 6,553,092 B1 | * | 4/2003 | Mattson et al. | 378/19 |
| 2006/0113483 A1 | * | 6/2006 | Sugihara et al. | 250/370.09 |
| 2007/0025518 A1 | * | 2/2007 | Levene et al. | 378/19 |
| 2007/0152159 A1 | * | 7/2007 | Short et al. | 250/505.1 |
| 2007/0235654 A1 | * | 10/2007 | Yahata et al. | 250/370.11 |

FOREIGN PATENT DOCUMENTS

| | | | |
|---|---|---|---|
| JP | 04002989 A | * | 1/1992 |
| JP | 09-127249 | | 5/1997 |
| JP | 2001-215281 | | 8/2001 |
| JP | 2006-145431 | | 6/2006 |
| JP | 2008-224624 | | 9/2008 |
| JP | 2008-272018 | | 11/2008 |
| JP | 2009-142398 | | 7/2009 |

OTHER PUBLICATIONS

Translation of JP 09-127248 A published on May 16, 1997.*
Office Action mailed Jan. 21, 2014 in Japanese Application No. 2010-097329.
Office Action mailed Jul. 1, 2014 in Japanese Application No. 2010-097329 filed Apr. 20, 2010.

* cited by examiner

*Primary Examiner* — Glen Kao
(74) *Attorney, Agent, or Firm* — Oblon, McClelland, Maier & Neustadt, L.L.P.

(57) ABSTRACT

An X-ray detector of an X-ray CT apparatus has a collimator, a plurality of scintillators, a light reflector and a plurality of photodiodes. The collimator has a threshold plate with a thickness Wc to eliminate scattered radiation from an X-ray. The plurality of scintillators emit light based on the X-ray. The light reflector is provided in a gap between adjacent scintillators of the plurality of scintillators. The plurality of photodiodes convert the light of each of the plurality of scintillators into the electric signal. The thickness Wc of the threshold plate mounted on the X-ray incident side of the adjacent scintillators, and a thickness Ws of the gap has a relationship shown in a following expression: Wc≥Ws.

8 Claims, 7 Drawing Sheets

X-RAY CT APPARATUS AND X-RAY DETECTOR

CROSS-REFERENCE TO RELATED APPLICATION

This application is based upon and claims the benefit of priority from Japanese Patent Application No. 2010-97329, filed on Apr. 20, 2010, the entire contents of which are incorporated herein by reference.

FIELD

The present embodiment relates to an X-ray CT apparatus having an X-ray detector and a data acquisition system (DAS), and to the X-ray detector.

BACKGROUND

X-ray CT apparatuses have an X-ray source and an X-ray detector arranged facing each other with an object therebetween. The X-ray detector includes a plurality of channels (M channels) of detection elements along a direction (a channel direction) perpendicular to a longitudinal direction of a tabletop as a body axis direction.

While various types of X-ray detectors may be employed, a scintillation detector, which can be small-sized, is typically used in the X-ray CT apparatus. Each detection element of the scintillation detector has a scintillator and an optical sensor such as a PD (photodiode). The scintillator absorbs X-rays collimated at a preceding stage to thereby produce light (fluorescence). The PD converts the light into an electric signal by the optical sensor, and outputs the electric signal to a DAS. A plurality of C-amp chips and A/D conversion chips are mounted on the DAS. The C-amp chip amplifies a voltage signal based on the electric signal. The A/D conversion chip converts the amplified signal into a digital signal. In the X-ray CT apparatus, the X-ray source emits an X-ray beam in a fan shape toward a section of the object, and each detection element of the X-ray detector converts the X-ray beam transmitted through a slice surface of the object into the electric signal. Transmission data can be thereby collected.

The C-amp chip and the A/D (analog to digital) conversion chip of the DAS are electronic parts. When the chips are exposed to X-rays (radiation) for a long period of time, trouble may occur on the DAS. Thus, the DAS is arranged (mounted) at a position not exposed to X-rays in a gantry (a rotation unit) of the X-ray CT apparatus.

In recent years, high integration or high-density packaging of electronic parts has been enabled, and a technique to integrally form the X-ray detector and the DAS (as a module) has been also developed to improve performance. When the X-ray detector and the DAS are integrally formed, however, the DAS is arranged on a side opposite to an X-ray incident side across the X-ray detector, that is, at a position exposed to X-rays not fully absorbed and thus leaking from the X-ray detector. The DAS is thereby exposed to X-rays not fully absorbed and thus leaking from the X-ray detector when the X-ray detector and the DAS are integrally formed, so that trouble such as a breakdown may occur on the DAS.

When the DAS is arranged at a position not exposed to X-rays in a structure where the X-ray detector and the DAS are integrally formed, the detection element of the X-ray detector and the DAS cannot be arranged in a tiling fashion.

BRIEF DESCRIPTION OF THE DRAWINGS

In accompanying drawings.

DETAILED DESCRIPTION

Figure 1:
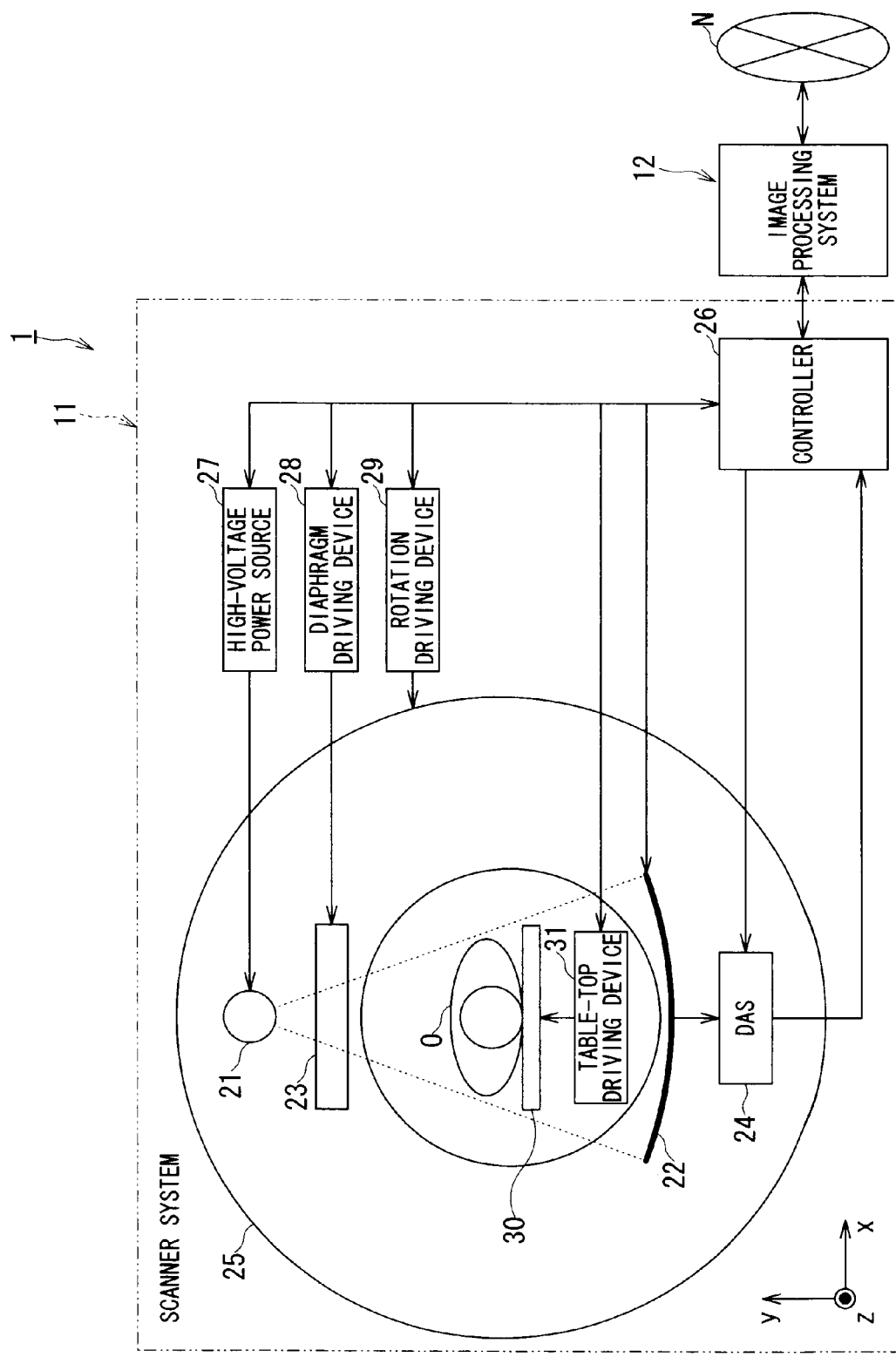
FIG. 1 is a hardware configuration diagram illustrating an X-ray CT apparatus according to the present embodiment.

An X-ray CT apparatus and an X-ray detector according to the present embodiment will be described by reference to the accompanying drawings.

To solve the above-described problems, the X-ray CT apparatus according to the present embodiment has: an X-ray source configured to generate an X-ray; an X-ray detector configured to acquire an electric signal based on the X-ray; and a data acquisition system arranged on a side opposite to an X-ray incident side across the X-ray detector, wherein the X-ray detector has: a collimator having a threshold plate with a thickness Wc to eliminate scattered radiation from the X-ray; a plurality of scintillators configured to emit light based on the X-ray; a light reflector provided in a gap between adjacent scintillators of the plurality of scintillators; and a plurality of photodiodes configured to convert the light of each of the plurality of scintillators into the electric signal, wherein the thickness Wc of the threshold plate mounted on the X-ray incident side of the adjacent scintillators, and a thickness Ws of the gap has a relationship shown in a following expression: Wc≥Ws.

To solve the above-described problems, the X-ray detector according to the present embodiment has: a collimator having a threshold plate with a thickness Wc to eliminate scattered radiation from an X-ray; a plurality of scintillators configured to emit light based on the X-ray; a light reflector provided in a gap between adjacent scintillators of the plurality of scintillators; and a plurality of photodiodes configured to convert the light of each of the plurality of scintillators into the electric signal, wherein the thickness Wc of the threshold plate mounted on the X-ray incident side of the adjacent scintillators, and a thickness Ws of the gap has a relationship shown in a following expression: Wc≥Ws.

There are various types of the X-ray CT apparatus of the present embodiment, such as a ROTATE/ROTATE type in which an X-ray tube and an X-ray detector rotate as one body around an object, a STATIONARY/ROTATE type in which a large number of detection elements are arrayed in a ring-shape, and only the X-ray tube rotates around the object, and the like. The present invention can be applied to any of those types. Hereafter, the ROTATE/ROTATE type which is currently in a mainstream position will be described.

Further, the current mainstream of the mechanism for converting incoming X-ray into electric charge includes an indirect conversion type in which X-ray is converted into light with a fluorescent body such as a scintillator, etc., and the light is converted into electric charge with a photoelectric conversion element such as a photodiode, etc., and a direct conversion type in which the generation of an electron-hole pair in a semiconductor and the transfer thereof to an electrode, that is, a photoconductive phenomenon is utilized.

In addition, in recent years, a progress has been made in the commercialization of a so-called multi-tube type X-ray CT apparatus, in which a plurality of pairs of the X-ray tube and the X-ray detector are mounted on a rotary ring, and the development of peripheral technologies thereof has been in progress. The X-ray CT apparatus of the present embodiment can be applied to either of a conventional single-tube type X-ray CT apparatus, or a multi-tube type X-ray CT apparatus. Here, description will be made supposing a single-tube type X-ray CT apparatus.

FIG. 1 is a hardware configuration diagram illustrating an X-ray CT apparatus according to the present embodiment.

FIG. 1 shows an X-ray CT apparatus 1 according to the present embodiment. The X-ray CT apparatus 1 mainly has a scanner system 11 and an image processing system 12. The scanner system 11 of the X-ray CT apparatus 1 is normally installed in an examination room, and generates X-ray transmission data on a shot area of an object (a human body) O. The image processing system 12 is normally installed in a control room next to the examination room, and generates projection data based on the transmission data to generate and display a reconstructed image.

The scanner system 11 of the X-ray CT apparatus 1 has an X-ray tube 21 as an X-ray source, an X-ray detector (a scintillation detector) 22, a diaphragm 23, a DAS 24, a rotation unit 25, a controller 26, a high-voltage power source 27, a diaphragm driving device 28, a rotation driving device 29, a table-top 30, and a table-top driving device (a table device) 31.

The X-ray tube 21 emits X-rays toward the X-ray detector 22 based on a tube voltage supplied from the high-voltage power source 27. The X-rays emitted from the X-ray tube 21 form a fan X-ray beam or a cone X-ray beam.

The X-ray detector 22 is a one-dimensional array-type X-ray detector, which includes a plurality of (M) channels of detection elements in a direction (a channel direction) perpendicular to a longitudinal direction of the table-top as a body axis direction, and one row of detection elements in a slice direction (a row direction). Alternatively, the X-ray detector 22 is a two-dimensional array-type X-ray detector 22 (also referred to as a multi-slice detector), which includes detection elements arranged in a matrix, that is, a plurality of (M) channels of detection elements in the channel direction perpendicular to the longitudinal direction of the table-top as the body axis direction, and a plurality of (N) rows of detection elements in the row direction. A case in which the X-ray detector 22 is the multi-slice detector will be described below. The X-ray detector 22 detects the X-rays emitted from the X-ray tube 21 and transmitted through the object O.

The diaphragm 23 regulates an emission range in the slice direction of the X-rays emitted from the X-ray tube 21 by the diaphragm driving device 28. To be more specific, the diaphragm driving device 28 regulates an opening of the diaphragm 23, so that the X-ray emission range in the slice direction can be changed.

The DAS 24 converts an electric signal of the transmission data detected by each detection element of the X-ray detector 22 into a voltage signal, amplifies the voltage signal, and converts the amplified signal into a digital signal. Output data from the DAS 24 is supplied to the image processing system 12 via the controller 26.

The rotation unit 25 is accommodated in a gantry (not shown) of the scanner system 11. The rotation unit 25 integrally holds the X-ray tube 21, the X-ray detector 22, the diaphragm 23, and the DAS 24. The rotation unit 25 can integrally rotate the X-ray tube 21, the X-ray detector 22, the diaphragm 23, and the DAS 24 around the object O with the X-ray tube 21 and the X-ray detector 22 facing each other.

The controller 26 includes a CPU (central processing unit), and a memory. The controller 26 conducts scanning by controlling the X-ray detector 22, the DAS 24, the high-voltage power source 27, the diaphragm driving device 28, the rotation driving device 29, and the table-top driving device 31 based on a control signal. The control signal is input from the image processing system 12.

The high-voltage power source 27 is controlled by the controller 26 to supply necessary power for emitting X-rays to the X-ray tube 21.

The diaphragm driving device 28 is controlled by the controller 26 to regulate the X-ray emission range in the slice direction of the diaphragm 23.

The rotation driving device 29 is controlled by the controller 26 to rotate the rotation unit 25 such that the rotation unit 25 is rotated around a hollow space while maintaining a positional relationship.

The table-top 30 can place the object O thereon.

The table-top driving device 31 is controlled by the controller 26 to move the table-top 30 along a z-axis direction. The rotation unit 25 has an opening in its center portion. The object O placed on the table-top 30 is inserted into the opening portion.

The image processing system 12 of the X-ray CT apparatus 1 is a computer-based device, and can communicate with a network N such as a hospital backbone LAN (local area network). Although not shown in the drawings, the image processing system 12 includes basic hardware such as a CPU, a memory, an HDD (hard disk drive), an input device, and a display device.

The image processing system 12 generates the projection data by performing correction processing (pre-processing) such as logarithmic conversion and sensitivity correction on raw data. The raw data is input from the DAS 24 of the scanner system 11. The image processing system 12 also eliminates scattered radiation from the projection data on which the pre-processing has been performed. The image processing system 12 eliminates scattered radiation based on a value of the projection data within the X-ray emission range. The image processing system 12 performs scattered radiation correction by reducing scattered radiation from target projection data to be subjected to the scattered radiation correction. The scattered radiation to be reduced is estimated from the magnitude of the value of the target projection data, or of projection data adjacent thereto. The image processing system 12 generates a reconstructed image based on the corrected projection data.

Figure 2:
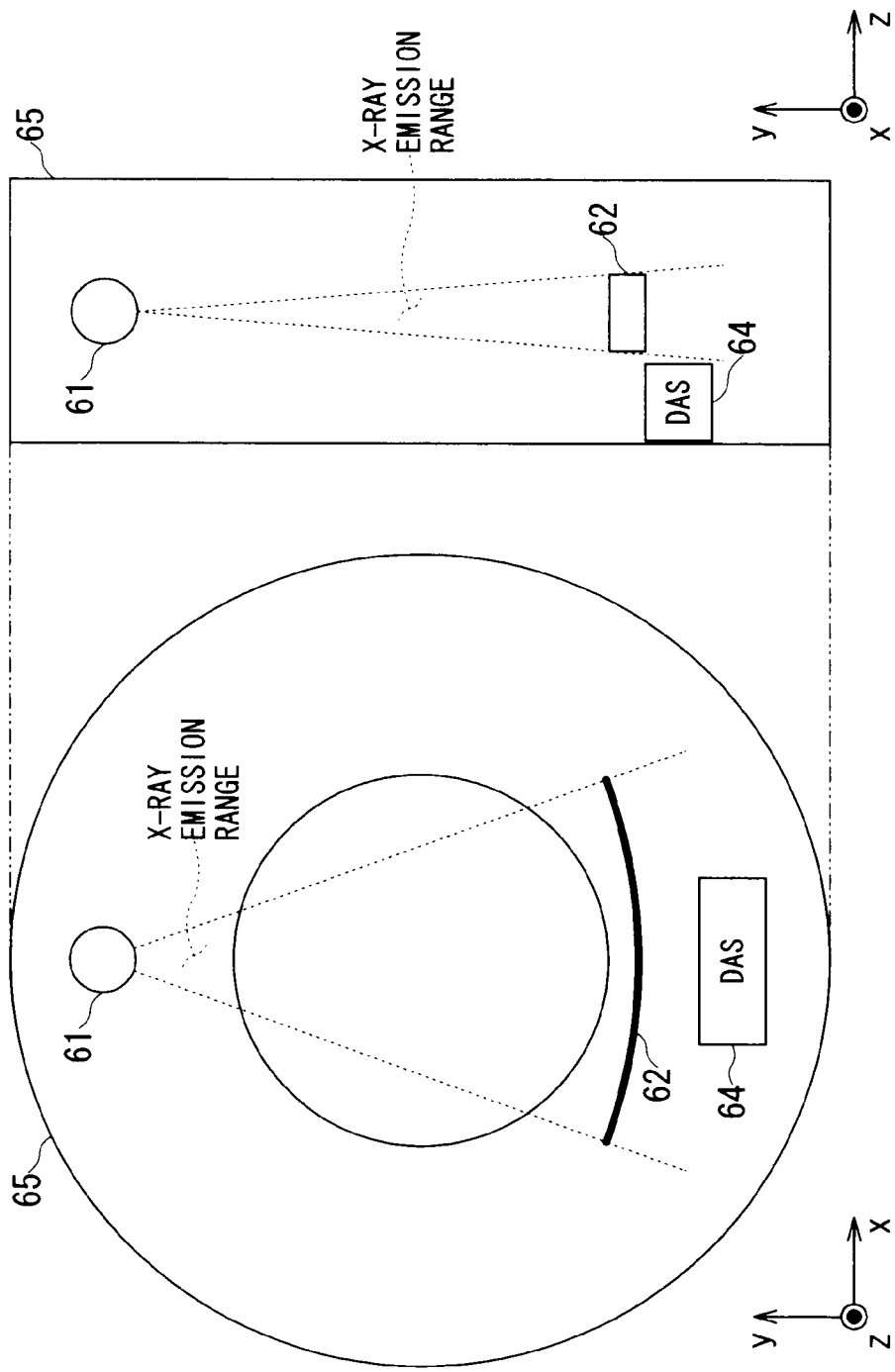
FIG. 2 is a side view illustrating a configuration of a rotation unit of a conventional X-ray CT apparatus.
Figure 3:
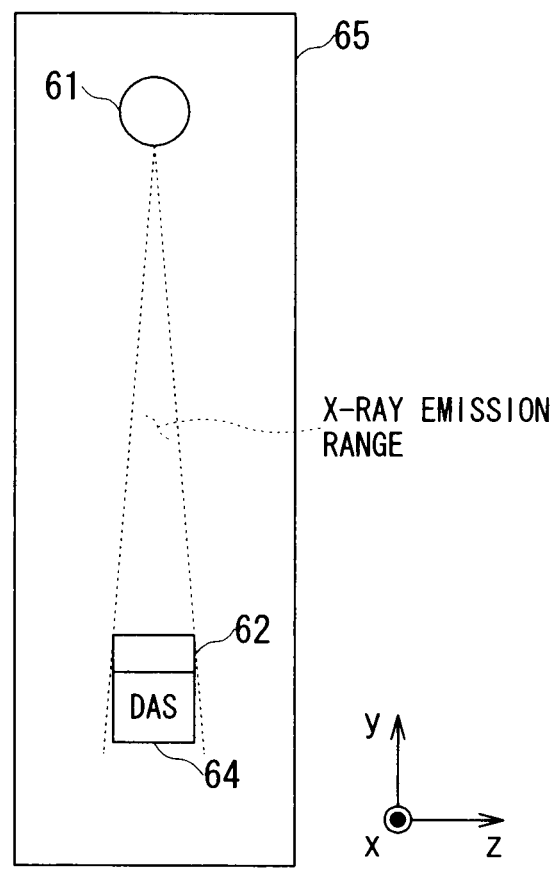
FIG. 3 a side view illustrating a configuration of a rotation unit of a conventional X-ray CT apparatus.
Figure 4:
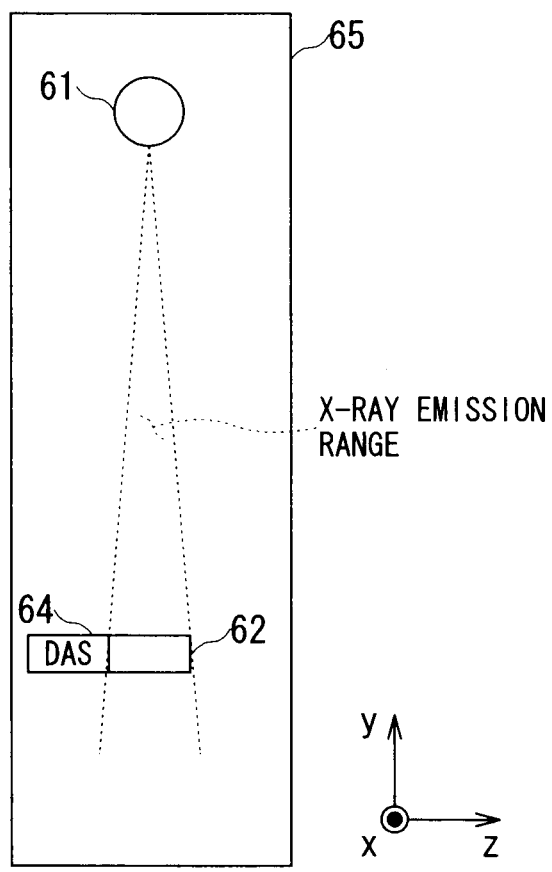
FIG. 4 a side view illustrating a configuration of a rotation unit of a conventional X-ray CT apparatus.

FIGS. 2-4 are a side view illustrating a configuration of a rotation unit of a conventional X-ray CT apparatus.

FIGS. 2-4 show an X-ray tube 61, an X-ray detector 62, a DAS 64, and a rotation unit 65 of the conventional X-ray CT apparatus. The X-ray tube 61, the X-ray detector 62, the DAS 64, and the rotation unit 65 each have the same functions as those of the X-ray tube 21, the X-ray detector 22, the DAS 24, and the rotation unit 25 of the X-ray CT apparatus 1 shown in FIG. 1.

A C-amp chip and an A/D conversion chip of the DAS 64 are electronic parts. When the chips are exposed to X-rays (radiation) for a long period of time, trouble such as breakdown may occur on the DAS 64. Thus, the DAS 64 is arranged (mounted) at a position not exposed to X-rays in the rotation unit 65 of the X-ray CT apparatus. The DAS 64 inputs an electric signal of transmission data detected by each detection element of the X-ray detector 62 via a signal cable.

In recent years, high integration or high-density packaging of electronic parts has been enabled, and a technique to integrally form the X-ray detector 62 and the DAS 64 (shown in FIG. 3) has been also developed to improve performance. When the X-ray detector 62 and the DAS 64 are integrally formed, however, the DAS 64 is arranged on a side opposite to an X-ray incident side across the X-ray detector 62, that is, at a position exposed to X-rays not fully absorbed and thus leaking from the X-ray detector 62. The DAS 64 is thereby exposed to X-rays not fully absorbed and thus leaking from the X-ray detector 62 when the X-ray detector 62 and the DAS 64 are integrally formed, so that trouble may occur on the DAS 64.

When the DAS 64 is arranged at a position not exposed to X-rays (shown in FIG. 4) in a structure where the X-ray detector 62 and the DAS 64 are integrally formed, the detection element of the X-ray detector 62 and the DAS 64 cannot be arranged in a tiling fashion.

A specific example of the X-ray CT apparatus 1 according to the present embodiment will be described below.

Figure 5:
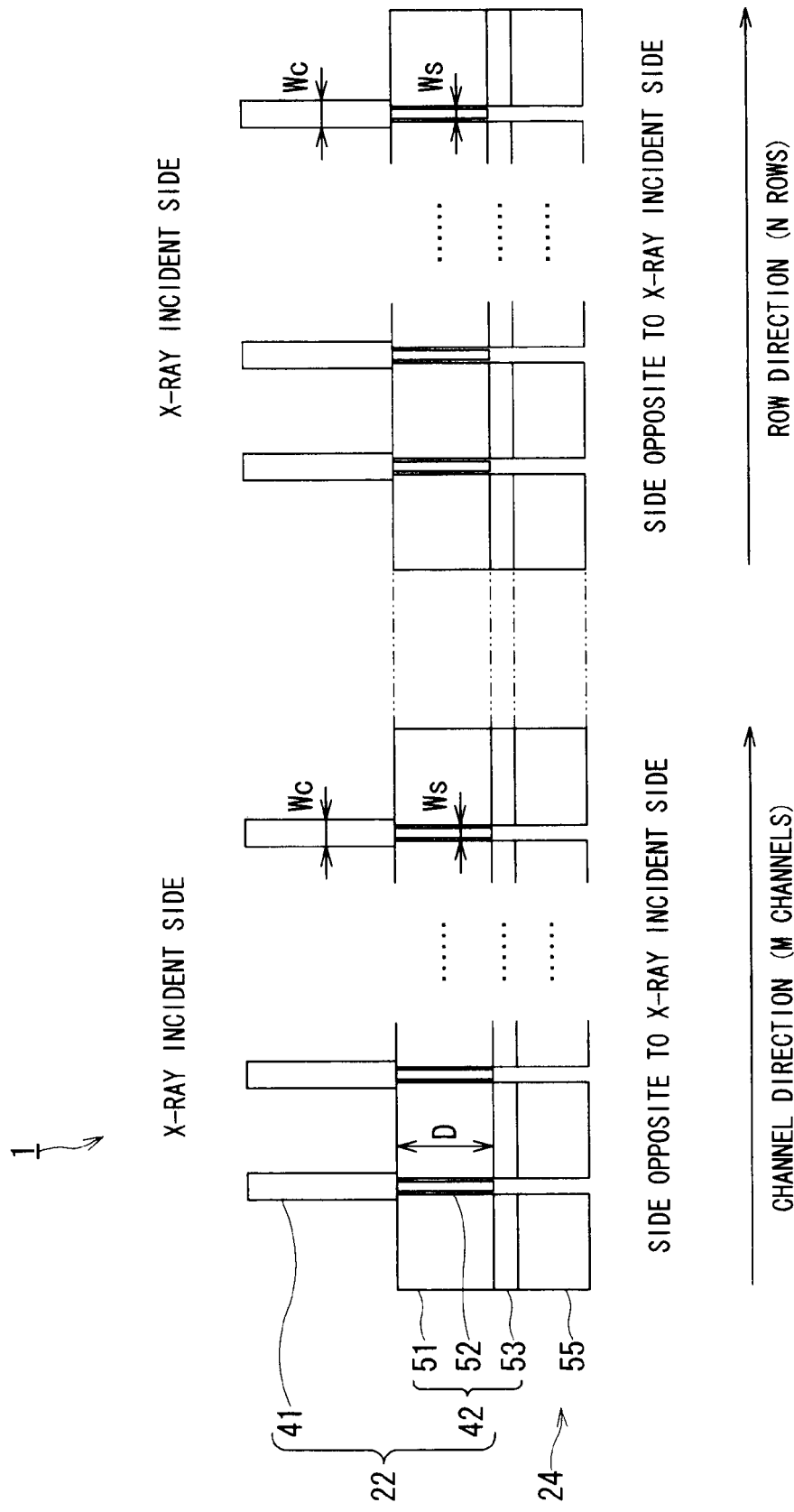
FIG. 5 is a side view illustrating a first configuration example of an X-ray detector and a DAS of the X-ray CT apparatus according to the present embodiment.

FIG. 5 is a side view illustrating a first configuration example of the X-ray detector 22 and the DAS 24 of the X-ray CT apparatus 1 according to the present embodiment.

FIG. 5 shows the multi-slice X-ray detector 22 and the DAS 24 as viewed from two side surfaces. The X-ray detector 22 includes a collimator 41, and M×N detection elements 42 corresponding to M channels×N rows. The collimator 41 has a threshold plate (a lead plate) with a thickness Wc to eliminate scattered radiation. The detection elements 42 generate an electric signal based on X-rays at a subsequent stage of the collimator 41. Each of the detection elements 42 includes a scintillator 51 having a thickness D, a light reflector (a separator) 52 and a PD 53. The light reflector is provided in a gap between the scintillator 51 and the scintillator 51 adjacent thereto to reflect light. The DAS 24 includes a plurality of DAS chips (C-amp chips and A/D conversion chips) 55 corresponding to the number of the detection elements 42 on a one-to-one basis, or a plurality of DAS chips 55 corresponding to the number of the detection elements 42 on a one-to-plural basis. FIG. 5 shows the DAS 24 in the former case. The threshold plate of the collimator 41 is mounted on the X-ray incident side of the adjacent scintillators.

A relationship between the thickness Wc of the threshold plate of the collimator 41, and a thickness Ws of the gap between the adjacent scintillators 51 shown in FIG. 5 is set as in the following expression (1).

$$Wc \geq Ws \quad (1)$$

When the collimator 41 is actually manufactured, a relationship between the thickness Wc of the threshold plate of the collimator 41 and a design thickness Ws' of the gap is taken into consideration based on the alignment (arrangement accuracy) of the scintillators 51 (the detection elements 42). The relationship between the thickness Wc of the threshold plate of the collimator 41 and the design thickness Ws' of the gap is set as in the following expression (2). Each alignment of two adjacent scintillators 51 (a displacement of each scintillator 51) forming the design thickness Ws' of the gap is represented as "d".

$$Wc \geq Ws' + 2d \quad (2)$$

If the thickness Wc of the collimator 41 is too large according to the above expressions (1) and (2), the scintillator 51 decreases in light-receiving capability (sensitivity). Thus, a value at which the scintillator 51 has enough light-receiving capability is selected as an upper limit of the thickness Wc of the collimator 41.

According to the above expressions (1) and (2), X-rays incident on the scintillator 51 can be blocked by the scintillator 51 having the thickness D large enough to block the X-rays, and X-rays to be transmitted through the gap (the light reflector 52) between the scintillators 51 can be blocked by the threshold plate of the collimator 41 having the thickness Wc. Therefore, in the first configuration example of the X-ray CT apparatus 1 according to the present embodiment which employs the above expressions (1) and (2), X-rays do not leak from the X-ray detector 22 to the side opposite to the X-ray incident side across the X-ray detector 22. Even when the X-ray detector 22 and the DAS 24 are integrally formed, the DAS 24 is not exposed to X-rays in the first configuration example of the X-ray CT apparatus 1 according to the present embodiment which employs the above expressions (1) and (2). It goes without saying that the collimator 41 has enough depth to block X-rays.

Figure 6:
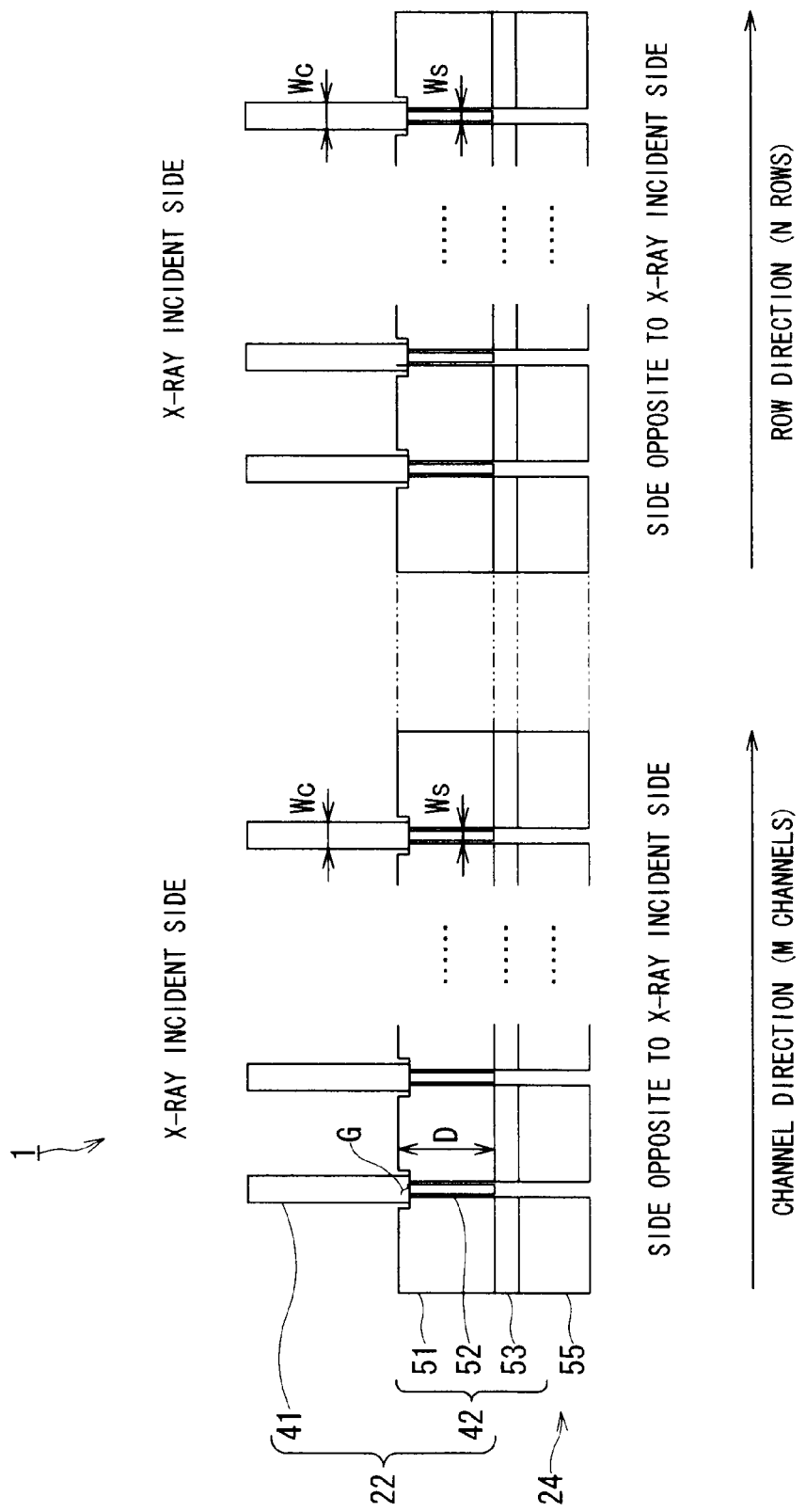
FIG. 6 is a side view illustrating a second configuration example of the X-ray detector and the DAS of the X-ray CT apparatus according to the present embodiment.

FIG. 6 is a side view illustrating a second configuration example of the X-ray detector 22 and the DAS 24 of the X-ray CT apparatus 1 according to the present embodiment.

FIG. 6 shows the X-ray detector 22 and the DAS 24 as viewed from two side surfaces in a similar manner to FIG. 5. A fitting (loose-fitting) groove G configured to mount the threshold plate of the collimator 41 thereon is provided on the X-ray incident side of the scintillator 51 of the X-ray detector 22 as shown in FIG. 6.

In the second configuration example of the X-ray CT apparatus 1 according to the present embodiment which employs the above expressions (1) and (2), X-rays do not leak from the X-ray detector 22 to the side opposite to the X-ray incident side across the X-ray detector 22 in a similar manner to the first configuration example of the X-ray CT apparatus 1 according to the present embodiment shown in FIG. 5. Even when the X-ray detector 22 and the DAS 24 are integrally formed, the DAS 24 is not exposed to X-rays in the second configuration example of the X-ray CT apparatus 1 according to the present embodiment which employs the above expressions (1) and (2).

Since the fitting groove G is provided on the X-ray incident side of the scintillator 51 as shown in FIG. 6, the threshold plate of the collimator 41 is easily positioned relative to the scintillator 51 when mounted thereon. A small gap may be possibly generated in a contact surface between the threshold plate of the collimator 41 and the scintillator 51 shown in FIG. 5. Thus, the fitting groove G is provided on the X-ray incident side of the scintillator 51 as shown in FIG. 6, so that scattered X-rays to be transmitted through the small gap in the contact surface between the threshold plate of the collimator 41 and the scintillator 51 can be fully blocked.

Figure 7:
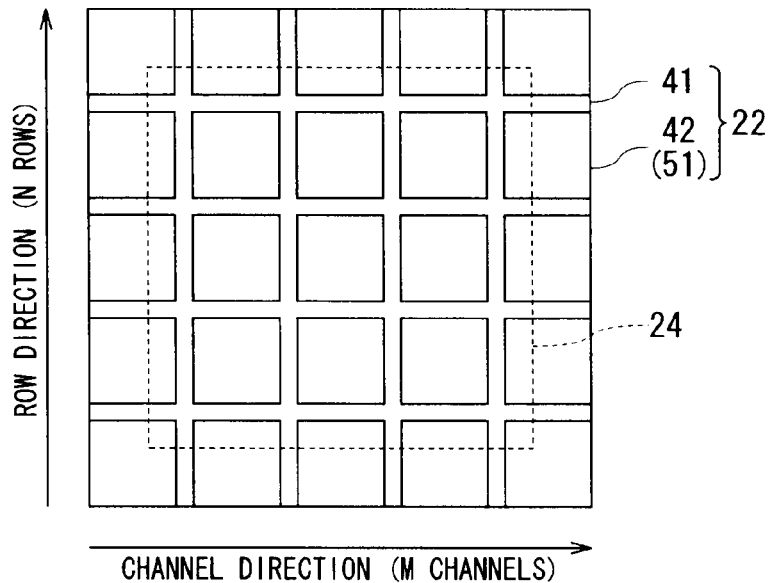
FIG. 7 is a top view illustrating a third configuration example of the X-ray detector and the DAS of the X-ray CT apparatus according to the present embodiment.

FIG. 7 is a top view illustrating a third configuration example of the X-ray detector 22 and the DAS 24 of the X-ray CT apparatus 1 according to the present embodiment.

FIG. 7 shows the two-dimensional array-type X-ray detector 22 having 5 channels×5 rows of detection elements 42, and the DAS 24.

The X-ray detector 22 shown in FIG. 7 includes the collimator 41 configured to eliminate scattered radiation, the M×N detection elements 42 configured to generate an electric signal based on X-rays at the subsequent stage of the collimator 41, and the DAS 24 in a similar manner to the configuration in FIG. 5. Each of the detection elements 42 includes the scintillator 51 having a thickness large enough to block X-rays, the light reflector, and the PD in a similar manner to the configuration in FIG. 5. The DAS 24 includes the plurality of DAS chips corresponding to the number of the detection elements 42 on a one-to-one basis, or the plurality of DAS chips corresponding to the number of the detection elements 42 on a one-to-plural basis in a similar manner to the configuration in FIG. 5.

The third configuration example of the X-ray CT apparatus 1 shown in FIG. 7 shows the case of Wc=Ws in the above expression (1).

In the third configuration example of the X-ray CT apparatus 1 according to the present embodiment which employs the above expressions (1) and (2), X-rays do not leak from the X-ray detector 22 to the side opposite to the X-ray incident side across the X-ray detector 22 in a similar manner to the first configuration example of the X-ray CT apparatus 1 according to the present embodiment shown in FIG. 5. Even when the X-ray detector 22 and the DAS 24 are integrally formed, the DAS 24 is not exposed to X-rays in the third configuration example of the X-ray CT apparatus 1 according to the present embodiment which employs the above expressions (1) and (2).

The third configuration example of the X-ray CT apparatus 1 according to the present embodiment shown in FIG. 7 may be also combined with the second configuration example of the X-ray CT apparatus 1 according to the present embodiment shown in FIG. 6. That is, the fitting groove may be provided on the X-ray incident side of the scintillator 51 in the third configuration example of the X-ray CT apparatus 1 according to the present embodiment.

Figure 8:
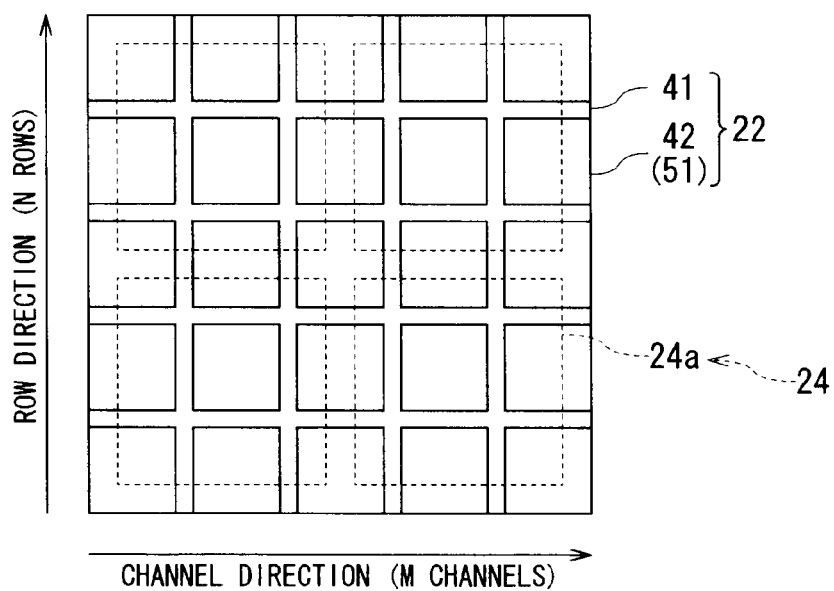
FIG. 8 is a top view illustrating a fourth configuration example of the X-ray detector and the DAS of the X-ray CT apparatus according to the present embodiment.

FIG. 8 is a top view illustrating a fourth configuration example of the X-ray detector 22 and the DAS 24 of the X-ray CT apparatus 1 according to the present embodiment.

FIG. 8 shows the two-dimensional array-type X-ray detector 22 having 5 channels×5 rows of detection elements 42, and the DAS 24.

The X-ray detector 22 shown in FIG. 8 includes the collimator 41 configured to eliminate scattered radiation, the M×N detection elements 42 configured to generate an electric signal based on X-rays at the subsequent stage of the collimator 41, and the DAS 24 in a similar manner to the configuration in FIG. 5. Each of the detection elements 42 include the scintillator 51 having a thickness large enough to block X-rays, the light reflector, and the PD in a similar manner to the configuration in FIG. 5. The DAS 24 includes a plurality of, for example, four DAS units 24a. Each of the DAS units 24a includes a plurality of DAS chips corresponding to the number of the detection elements 42 on a one-to-one basis, or a plurality of DAS chips corresponding to the number of the detection elements 42 on a one-to-plural basis.

The fourth configuration example of the X-ray CT apparatus 1 shown in FIG. 8 shows the case of Wc-Ws in the above expression (1).

In the fourth configuration example of the X-ray CT apparatus 1 according to the present embodiment which employs the above expressions (1) and (2), X-rays do not leak from the X-ray detector 22 to the side opposing the X-ray incident side of the X-ray detector 22 in a similar manner to the first configuration example of the X-ray CT apparatus 1 according to the present embodiment shown in FIG. 5. Even when the X-ray detector 22 and the DAS 24 are integrally formed, the DAS 24 is not exposed to X-rays in the fourth configuration example of the X-ray CT apparatus 1 according to the present embodiment which employs the above expressions (1) and (2).

The fourth configuration example of the X-ray CT apparatus 1 according to the present embodiment shown in FIG. 8 may be also combined with the second configuration example of the X-ray CT apparatus 1 according to the present embodiment shown in FIG. 6. That is, the fitting groove may be provided on the X-ray incident side of the scintillator 51 in the fourth configuration example of the X-ray CT apparatus 1 according to the present embodiment.

In the X-ray CT apparatus 1 according to the present embodiment, even when the X-ray detector 22 and the DAS 24 are integrally formed, trouble such as a breakdown of the DAS 24 due to X-rays leaking from the X-ray detector 22 can be avoided.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
an X-ray source configured to generate an X-ray;
an X-ray detector configured to acquire an electric signal based on the X-ray; and
a data acquisition system arranged on a side opposite to an X-ray incident side across the X-ray detector, the data acquisition system including a plurality of amp chips each amplifying the electric signal, and a plurality of A/D conversion chips each converting the amplified electric signal into a digital signal and outputting the digital signal to an image processing system, wherein
the X-ray detector comprises:
a collimator configured to absorb the X-ray;
a plurality of scintillators configured to emit light resulting from incidence of the X-ray, the plurality of scintillators being provided so that a gap between adjacent scintillators of the plurality of scintillators is an extension of a gap between adjacent amp chips of the plurality of amp chips and of a gap between adjacent A/D conversion chips of the plurality of A/D conversion chips;
a light reflector provided in a gap between adjacent scintillators of the plurality of scintillators; and
a plurality of photodiodes configured to convert the light emitted by the plurality of scintillators into the electric signal.

2. The X-ray CT apparatus according to claim 1, wherein the plurality of scintillators, the plurality of photodiodes, and the data acquisition system are integrally formed.

3. The X-ray CT apparatus according to claim 1, wherein the collimator includes a plurality of threshold plates, and the plurality of threshold plates is formed in a matrix.

4. The X-ray CT apparatus according to claim 1, wherein the collimator includes a plurality of threshold plates with a thickness Wc,
the thickness Wc, a designed thickness Ws' of the gap between the adjacent scintillators and a displacement d of the scintillator of the plurality of scintillators have a relationship shown in a following transformed expression:

$$Wc \geq Ws' + 2d.$$

5. The X-ray CT apparatus according to claim 1, wherein at least one of the plurality of scintillators forms grooves on both sides in a channel direction, thereby forming a convex shape.

6. The X-ray CT apparatus according to claim 5, wherein at least one of the plurality of scintillators forms, when the X-ray detector is a two-dimensional detector in a channel direction and in a row direction, grooves on both sides in the channel direction and on both sides in the row direction, thereby forming a convex shape.

7. The X-ray CT apparatus according to claim 6, wherein the collimator includes a plurality of threshold plates, and the plurality of threshold plates placed on the grooves are formed of a grid in the channel direction and in the row direction.

8. The X-ray CT apparatus according to claim 1, wherein the collimator includes a plurality of threshold plates, each scintillator of the plurality of scintillators forms a groove on an X-ray incident side and in a position facing the gap with adjacent scintillator, and each threshold plate of the plurality of threshold plates contacts both a bottom of the groove of the each scintillator and a bottom of the groove of the adjacent scintillator, a width of the each threshold plate being longer than a width of the gap between the each scintillator and the adjacent scintillator.

\* \* \* \* \*